(12) United States Patent
Mathonnet

(10) Patent No.: US 11,406,254 B2
(45) Date of Patent: Aug. 9, 2022

(54) SURGICAL DEVICES AND SYSTEMS FOR MINIMALLY-INVASIVE VESSEL-HARVESTING AND OTHER SURGICAL PROCEDURES

(71) Applicant: COVIDIEN LP, Mansfield, MA (US)

(72) Inventor: Olivier Mathonnet, Boulogne Billancourt (FR)

(73) Assignee: Covidien LP, Mansfield, MA (US)

( * ) Notice: Subject to any disclaimer, the term of this patent is extended or adjusted under 35 U.S.C. 154(b) by 210 days.

(21) Appl. No.: 16/458,581

(22) Filed: Jul. 1, 2019

(65) Prior Publication Data

US 2020/0022572 A1 Jan. 23, 2020

Related U.S. Application Data

(60) Provisional application No. 62/702,165, filed on Jul. 23, 2018.

(51) Int. Cl.
| | | |
|---|---|---|
| A61B 1/313 | (2006.01) | |
| A61B 1/05 | (2006.01) | |
| A61B 1/06 | (2006.01) | |
| A61B 17/02 | (2006.01) | |
| A61B 1/00 | (2006.01) | |
| A61B 17/00 | (2006.01) | |

(52) U.S. Cl.
CPC .......... *A61B 1/313* (2013.01); *A61B 1/00052* (2013.01); *A61B 1/051* (2013.01); *A61B 1/0676* (2013.01); *A61B 17/02* (2013.01); *A61B 2017/00057* (2013.01); *A61B 2017/00424* (2013.01); *A61B 2560/0456* (2013.01)

(58) Field of Classification Search
CPC .............................................. A61B 2560/0456
USPC ................................................... 600/188-245
See application file for complete search history.

(56) References Cited

U.S. PATENT DOCUMENTS

| | | | |
|---|---|---|---|
| 5,769,782 A | * | 6/1998 | Phan ................... A61B 17/0206 600/202 |
| 6,139,489 A | | 10/2000 | Wampler et al. |
| 6,193,653 B1 | | 2/2001 | Evans et al. |
| 6,322,499 B1 | | 11/2001 | Evans et al. |
| 6,387,043 B1 | | 5/2002 | Yoon |
| 7,077,803 B2 | | 7/2006 | Kasahara et al. |
| 8,753,365 B2 | | 6/2014 | Gerrah et al. |
| 9,492,065 B2 | | 11/2016 | Tesar et al. |
| 9,655,673 B2 | | 5/2017 | McCullough, Jr. et al. |
| 2003/0130674 A1 | | 7/2003 | Kasahara et al. |
| 2011/0082345 A1 | * | 4/2011 | Surti ................... A61B 17/3423 600/210 |
| 2013/0158345 A1 | | 6/2013 | Majlessi |
| 2015/0025324 A1 | * | 1/2015 | Wan ....................... A61B 17/02 600/245 |

(Continued)

*Primary Examiner* — Eduardo C Robert
*Assistant Examiner* — Tara Rose E Carter
(74) *Attorney, Agent, or Firm* — Carter, DeLuca & Farrell LLP

(57) ABSTRACT

A visualization tissue retractor includes a handle defining a proximal end portion and a distal end portion, a dock extending from the proximal end portion of the handle and configured to receive a portable display device, a retractor arm extending from the distal end portion of the handle and defining a guide track disposed along at least a portion of a length thereof, and a surgical camera assembly engaged with the guide track and configured to slide therealong.

20 Claims, 2 Drawing Sheets

(56) References Cited

U.S. PATENT DOCUMENTS

2015/0112146 A1\* 4/2015 Donaldson ......... A61B 1/00032
600/188
2016/0128556 A1\* 5/2016 Lai ..................... A61B 1/00124
600/188
2016/0242637 A1\* 8/2016 Tydlaska ............ A61B 1/00101

\* cited by examiner

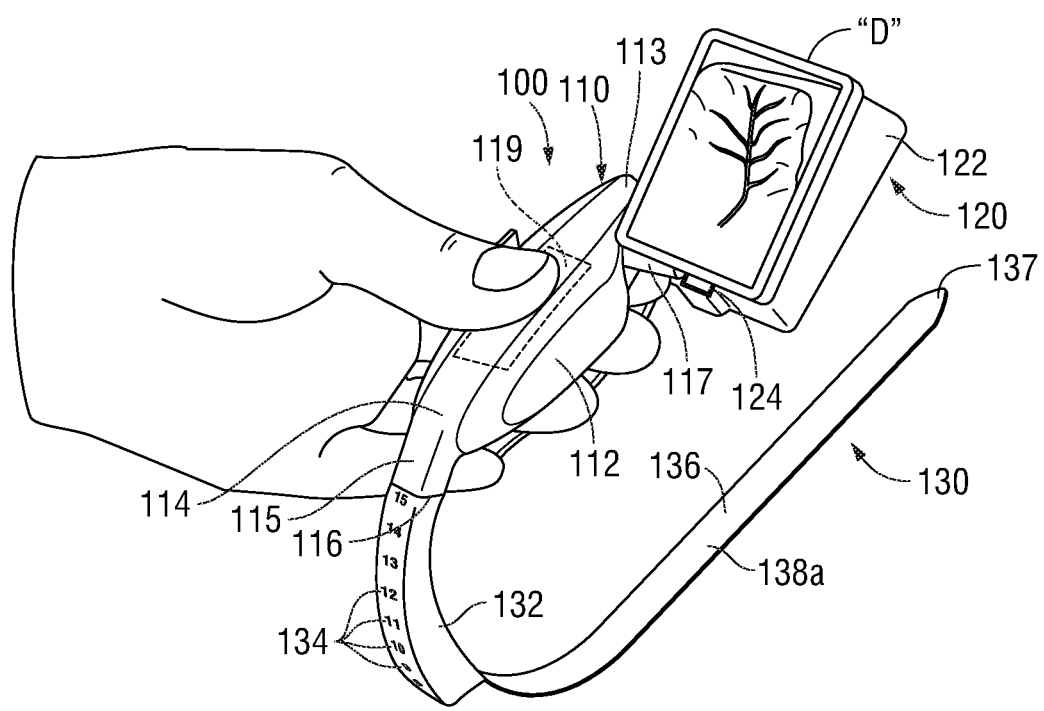
FIG. 1
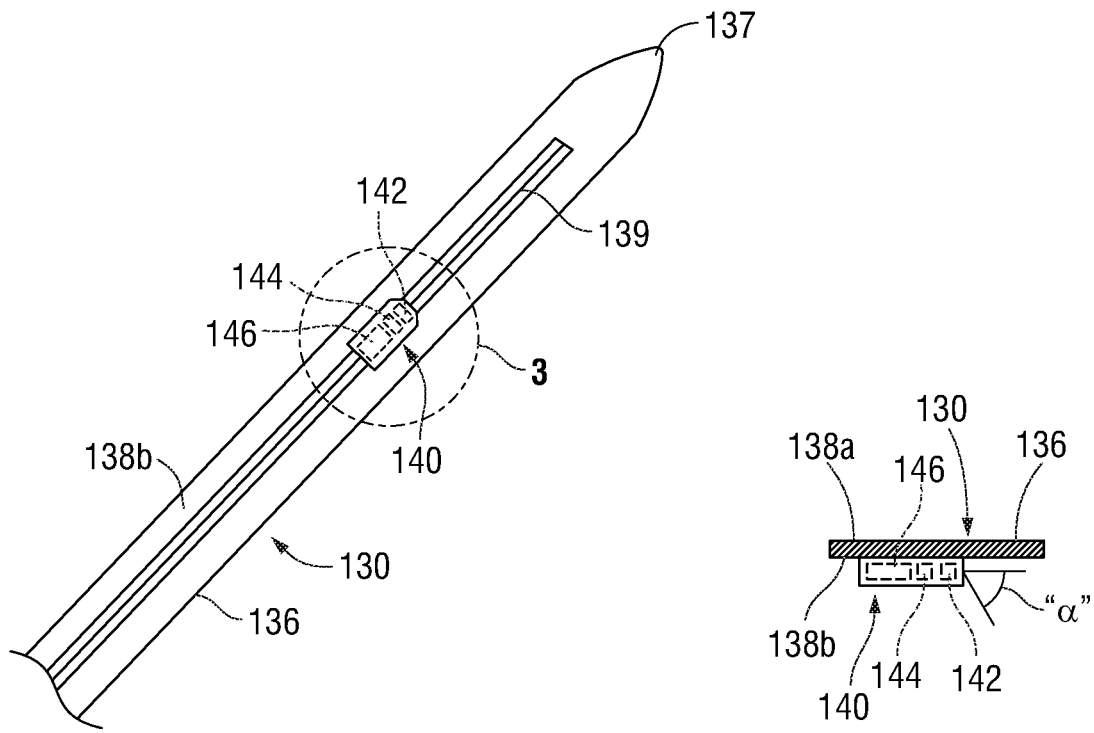
FIG. 2
FIG. 3

SURGICAL DEVICES AND SYSTEMS FOR MINIMALLY-INVASIVE VESSEL-HARVESTING AND OTHER SURGICAL PROCEDURES

CROSS REFERENCE TO RELATED APPLICATION

The present application claims the benefit of and priority to U.S. Provisional Application Ser. No. 62/702,165, filed on Jul. 23, 2018 the entire contents of which are incorporated herein by reference.

BACKGROUND

Technical Field

The present disclosure relates to surgical instruments and methods. More specifically, the present disclosure relates to surgical devices and systems for minimally-invasive vessel-harvesting and other surgical procedures.

Background of Related Art

Numerous surgical procedures have been developed to replace veins and arteries. Coronary bypass surgery, for example, utilizes a vessel harvested from elsewhere in the body and grafted into place, e.g., between the aorta and a coronary artery, to bypass a point of blockage in the coronary artery.

Vessel-harvesting has traditionally required skin incisions as long as the length of the vessel to be removed. However, this technique produces long scars and may result in a lengthy, difficult recovery from the harvesting procedure. More recently, less-invasive techniques have been developed such as, for example, minimally-invasive vessel-harvesting utilizing an endoscope or guide device incorporating an endoscope. In such procedures, the endoscope or guide device is directed towards the vessel to be harvested, the vessel is held with a grasper introduced through the endoscope or guide device, connective tissue is dissected from around the vessel, and the vessel is ligated, transected, and ultimately removed through the endoscope or guide device. The vessel-harvesting procedure is aided by use of an endoscopic video tower, including imagine processing and display capability, that is connected to the endoscope to provide visualization into the internal surgical site.

After harvesting, the removed vessel is prepared for implantation into the graft site.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a visualization tissue retractor including a handle, a dock, a retractor arm, and a surgical camera assembly. The handle defines a proximal end portion and a distal end portion. The dock extends from the proximal end portion of the handle and is configured to receive a portable display device. The retractor arm extends from the distal end portion of the handle and defines a guide track disposed along at least a portion of a length thereof. The surgical camera assembly is engaged with the guide track and configured to slide therealong.

In an aspect of the present disclosure, the surgical camera assembly includes a camera and a light source.

In another aspect of the present disclosure, the dock includes an electrical connection interface configured to electrically couple to the portable display device.

In another aspect of the present disclosure, the retractor arm defines a generally U-shaped configuration having a concave side and a convex site, a proximal portion, and a distal portion. The guide track is disposed along at least a portion of a length of the distal portion on the convex side thereof.

In still another aspect of the present disclosure, at least one of the handle or the surgical camera assembly includes a motor configured to drive movement of the surgical camera assembly along the guide track. Alternatively, the surgical camera assembly may be manually movable along the guide track, e.g., via a suitable actuator disposed on the handle or the retractor arm.

In yet another aspect of the present disclosure, at least one of the handle or the surgical camera assembly includes a battery configured to power the surgical camera assembly.

In still yet another aspect of the present disclosure, the surgical camera assembly includes a rotatable surgical camera.

In another aspect of the present disclosure, the retractor arm is slidable relative to the handle between a retracted position and an extended position.

In another aspect of the present disclosure, the retractor arm includes indicia disposed thereon configured to indicate an insertion depth of the retractor arm to a user.

A system provide in accordance with aspects of the present disclosure includes a portable display device and a visualization tissue retractor configured similar to any of the aspects of the visualization tissue retractor detailed above or otherwise herein.

In an aspect, the surgical camera assembly is configured to communicate with the portable display device such that the portable display device displays a video feed from a surgical camera of the surgical camera assembly.

In another aspect, the portable display device is configured to enable a user to control operation of the surgical camera assembly from the portable display device.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and:

FIG. 1 is a perspective view of a visualization tissue retractor provided in accordance with the present disclosure, shown grasped by a user, and configured for use in a minimally-invasive vessel-harvesting procedure;

FIG. 2 is a perspective, under-side view of a distal portion of a retractor arm of the visualization tissue retractor of FIG. 1;

FIG. 3 is a side view of the area of detail indicated as "3" in FIG. 2; and

DETAILED DESCRIPTION

Figure 4:
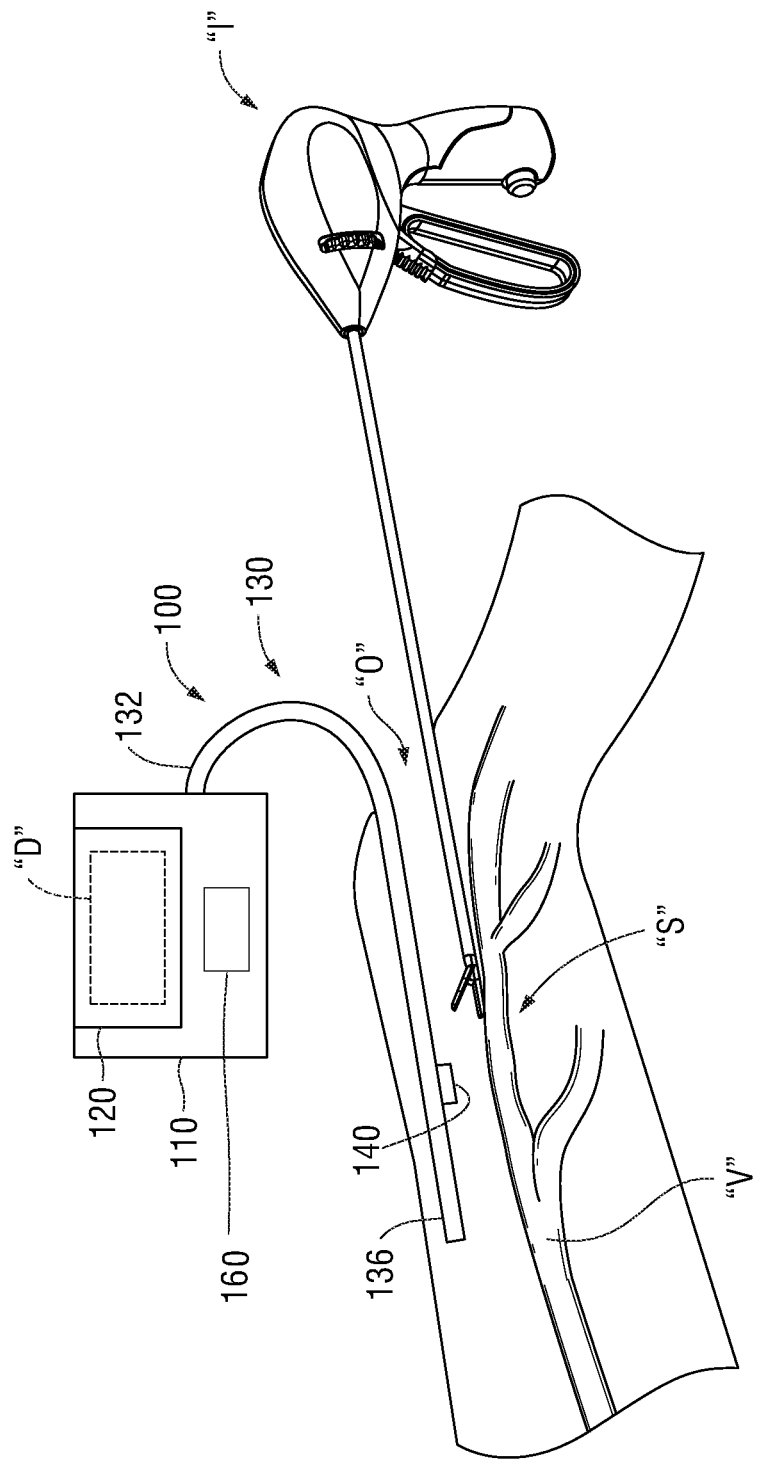
FIG. 4 is a schematic illustration of a surgical system provided in accordance with the present disclosure including the visualization tissue retractor of FIG. 1 and an endoscopic electrosurgical instrument, shown in use during a vessel-harvesting procedure.

Turning to FIG. 1, a visualization tissue retractor provided in accordance with the present disclosure and configured for use in a minimally-invasive vessel-harvesting procedure is shown identified by reference numeral 100. Visualization tissue retractor 100 generally includes a handle 110, a dock 120, a retractor arm 130, and a surgical camera assembly 140. Visualization tissue retractor 100 may be configured as a single use, disposable component or a sterilizable, reusable component.

Handle 110 is configured to be grasped with a single hand of a user and may include protrusions, indentations, or other features to facilitate ergonomic grasping of handle 110. Handle 110 defines a body 112 including a proximal end portion 113 and a distal end portion 114. A distal extension 115 defining a lumen 116 extends from distal end portion 114 of body 112 of handle 110, while a proximal extension 117 extends from proximal end portion 113 of body 112 of handle 110.

Proximal extension 117 of handle 110 extends from proximal end portion 113 of body 112 of handle 110 to dock 120. Dock 120 may be fixedly coupled to proximal extension 117 or may be movably coupled thereto such as, for example, via a pivoting connecting enabling dock 120 to tilt relative to handle 110. Dock 120 includes a support surface 122 and, in embodiments, an electrical connection interface 124. Support surface 122 is configured to removably support a portable display device "D" (or various different portable displace devices) such as for example, a tablet (e.g., an iPad®, available from Apple, Inc. of Cupertino, Calif., USA), a smart phone, etc. Electrical connection interface 124 may be a physical-connection interface configured to physically connect to a corresponding port associated with the portable display device "D" to establish electrical communication therebetween such as, for example, a USB Port, a Display Port, a PS/2 Port, an eSATA Port, a Lightening Port, etc. Alternatively or additionally, electrical connection interface 124 may wirelessly connect with the portable display device "D" to establish electrical communication therebetween such as, for example, via Bluetooth™ communication, near-field communication, infrared communication, RF communication, etc. The electrical communication between the portable display device "D" and electrical connection interface 124 (whether via physical connection and/or wirelessly) enables the transmission of power and/or control signals between portable display device "D" and surgical camera assembly 140 of visualization tissue retractor 100 either directly or via handle 110 and/or retractor arm 130 of visualization tissue retractor 100. In embodiments, electrical connection interface 124 may be omitted and power and/or control signals wirelessly communicated to surgical camera assembly 140 (FIGS. 2 and 3) without handle 110 and retractor arm 130 serving as an intermediary. In additional or alternative embodiments, a sterile bag (not shown) may be used with dock 120 to surround the portable display device "D" engaged thereon, thus maintaining a sterile field despite use of a non-sterile portable display device "D."

In embodiments, handle 110 may include a control unit 119 disposed therein including a processor and non-transitory computer-readable storage medium storing instructions to be executed by the processor, one or more motors, a transmitter/receiver, and/or a power source. Alternatively or additionally, a control unit 146 is provided in surgical camera assembly 140, as detailed below. Control unit 119 of handle 110, in embodiments where provided, is electrically coupled to electrical connection interface 124 for communicating with the portable display device "D" and/or is configured to wirelessly communicate with the portable display device "D" directly. Control unit 119 is further configured to communicate with surgical camera assembly 140, thus establishing communication between the portable display device "D" and surgical camera assembly 140.

Continuing with reference to FIG. 1, distal extension 116 of handle 110 extends from distal end portion 114 of body 112 of handle 110 and receives a proximal portion 132 of retractor arm 130 within lumen 117 thereof. Proximal portion 132 may be slidably received within lumen 117 to enable retractor arm 130 to slide relative to handle 110 between an extended position, wherein proximal portion 132 of retractor arm 130 extends further from distal extension 116 of handle 110 and a retracted position, wherein proximal portion 132 of retractor arm 130 is retracted further into lumen 117 of distal extension 116 of handle 110. Alternatively, proximal portion 132 may be fixedly engaged within lumen 117, e.g., via an adhesive, overmolding of handle 110 about proximal portion 132, or in any other suitable manner. Proximal portion 132 of retractor arm 130, in embodiments, includes indicia 134 disposed thereon to indicate to a user the extent to which retractor arm 130 extends into the internal surgical site "S" (FIG. 4).

Retractor arm 130 defines a generally U-shaped configuration wherein proximal portion 132 defines one upright portion of the generally U-shaped configuration of retractor arm 130 and wherein a distal portion 136 of retractor arm 130 defines the other upright portion of the generally U-shaped configuration. Proximal portion 132 and/or distal portion 136 may define part or all of the curved base interconnecting the uprights of the generally U-shaped retractor arm 130, and/or may otherwise define a curvature therealong and/or extend different lengths despite the generally U-shaped configuration of retractor arm 130.

With additional reference to FIG. 2, distal portion 136 of retractor arm 130 is configured for insertion through an opening "O" in tissue and into the internal surgical site "S" (see FIG. 4) and defines an elongated, plate-like configuration such as, for example, similar to a letter opener, to facilitate insertion in the internal surgical site "S" (FIG. 4). To this end, distal portion 136 may define a tapered distal tip 137 tapering to a blunt distal end to facilitate insertion through tissue without damaging tissue. However, other configurations are also contemplated.

Distal portion 136 of retractor arm 130 defines an upper-face 138a and an opposed under-face 138b. Upper-face 138a of distal portion 136 is disposed on the inner, concave side of the generally U-shaped retractor arm 130 while under-face 138b is disposed on the outer, convex side of the generally U-shaped retractor arm 130. A guide track 139 is defined on under-face 138b of distal portion 136 and extends along at least a portion of the longitudinal length thereof.

Referring also to FIG. 3, surgical camera assembly 140 is slidably engaged on guide track 139 and is configured to move longitudinally relative to under-face 138b of distal portion 136 of retractor arm 130 along guide track 139. Surgical camera assembly 140 includes a camera 142 and a light source 144 and, in embodiments, also includes a control unit 146. A motor of control unit 146 of surgical camera assembly 140 or a motor of control unit 119 of handle 110 is configured to drive movement of surgical camera assembly 140 along guide track 139 to achieve any suitable longitudinal position of surgical camera assembly 140 along guide track 139. Alternatively, an actuator 160 (FIG. 4) may be disposed on handle 120 or retractor arm 130 and operably coupled to surgical camera assembly 140, e.g., via one or more drive cables, links, shafts, etc., to enable manual movement of surgical camera assembly 140 along guide track 139 in response to movement, e.g., pivoting, sliding, rotating, etc., of actuator 160 (FIG. 4) relative to handle 120 and/or retractor arm 130.

Camera 142 is configured to obtain video and/or still images of the internal surgical site "S" (FIG. 4) and may be configured to rotate through an angle "a" of about 90°, in other embodiments, of about 60° and, in still other embodiments, of about 30°, although other angles are also contemplated. A motor of control unit 146 and/or a motor of control unit 119 of handle 110 is configured to drive rotation of camera 142 to achieve any suitable position within the range of rotation of angle "a." A power source, e.g. a battery, of control unit 146 and/or of control unit 119 of handle 110 is configured to power camera 142 and/or the motor driving rotation of camera 142. Alternatively, portable display device "D" or an external power source (not shown) may be configured to power camera 142 and/or the motor driving rotation of camera 142

Light source 144, e.g., one or more LED's, is configured to illuminate the internal surgical site "S" (FIG. 4) to facilitate visualization thereof with camera 142 and may be powered via a power source, e.g. a battery, of control unit 146 and/or of control unit 119 of handle 110, via portable display device "D," or via an external power source (not shown).

In embodiments where provided, control unit 146 of surgical camera assembly 140 includes a processor and non-transitory computer-readable storage medium storing instructions to be executed by the processor, one or more motors, a transmitter/receiver, and/or a power source. Control unit 146, is electrically coupled to electrical connection interface 124 for communicating with the portable display device "D," is configured to wirelessly communicate with the portable display device "D" directly, and/or is electrically coupled (wired or wirelessly) to control unit 119 which, in turn, is configured to communicate (wired or wirelessly) with portable display device "D" and surgical camera assembly 140.

Referring still to FIGS. 1-3, as detailed above, surgical camera assembly 140 may be powered locally, e.g., via a power source of control until 146 of surgical camera assembly 140, or may be powered remotely, e.g., via a power source of control unit 119 of handle 110, an external power source, or the portable display device "D." Likewise, surgical camera assembly 140 may be driven locally, e.g., via a motor of control until 146 of surgical camera assembly 140, or may be driven remotely, e.g., via a motor of control unit 119 of handle 110. In any of the above configurations, an application running on portable display device "D" enables communication (wired or wireless) between portable display device "D" and the appropriate components(s), e.g., of control assembly 119, control assembly 146, and/or other component(s), to enable a user to control operation and movement of surgical camera assembly 140 and also provides a display of the video and/or still image feed from camera 142 of surgical camera assembly 140.

With reference to FIG. 4, in use, distal portion 136 of retractor arm 130 of visualization tissue retractor 100 is inserted through the opening "O" in tissue and into the internal surgical site "S" to establish a passageway into the internal surgical site "S" and provide a guide path along the passageway. Thereafter, a surgical instrument "I" for performing the vessel harvesting procedure such as, for example, the endoscopic electrosurgical instrument described in commonly-owned U.S. Pat. No. 9,655,673, the entire contents of which is hereby incorporate herein by reference, is advanced into the internal surgical site "S" along and guided by distal portion 136 of retractor arm 130 of visualization tissue retractor 100 to the vessel "V" to be harvested and/or other tissue within the internal surgical site "S."

During positioning of visualization tissue retractor 100 and/or surgical instrument "I," surgical camera assembly 140 may be moved longitudinally along guide track 139 of distal portion 136 of retractor arm 130 and/or camera 142 rotated such that the user can visualize, on portable display device "D," the insertion of visualization tissue retractor 100 and/or surgical instrument "I." Surgical camera assembly 140 may further be moved longitudinally and/or camera 142 rotated during the harvesting of the vessel "V" to enable visualization on portable display device "D" and facilitate performance of the various surgical tasks associated with harvesting the vessel "V" from within the internal surgical site "S."

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A visualization tissue retractor, comprising:
    a handle defining a proximal end portion and a distal end portion, the distal end portion defining a lumen therein;
    a dock extending from the proximal end portion of the handle, the dock configured to receive a portable display device;
    a retractor arm extending from the distal end portion of the handle, a proximal portion of the retractor arm slidably received within the lumen to enable the retractor arm to slide relative to the handle between a retracted position and an extended position, the retractor arm having opposed first and second faces, one of the first or second faces defining a guide track disposed on a central portion thereof in laterally spaced relation relative to side edges of the retractor arm and extending along at least a portion of a longitudinal length thereof; and
    a surgical camera assembly engaged with the guide track and configured to slide therealong, the surgical camera assembly including a rotatable surgical camera.

2. The visualization tissue retractor according to claim 1, wherein the surgical camera assembly includes a light source.

3. The visualization tissue retractor according to claim 1, wherein the dock includes an electrical connection interface configured to electrically couple to the portable display device.

4. The visualization tissue retractor according to claim 1, wherein the retractor arm defines a generally U-shaped configuration with the first face of the retractor arm being at least partially concave and the second face of the retractor arm being at least partially convex, and wherein the guide track is disposed along a distal portion of the retractor arm on the second face thereof.

5. The visualization tissue retractor according to claim 1, wherein at least one of the handle or the surgical camera assembly includes a motor configured to drive movement of the surgical camera assembly along the guide track.

6. The visualization tissue retractor according to claim 1, wherein at least one of the handle or the surgical camera assembly includes a battery configured to power the surgical camera assembly.

7. The visualization tissue retractor according to claim 1, wherein the retractor arm includes indicia disposed thereon configured to indicate an insertion depth of the retractor arm to a user.

8. The visualization tissue retractor according to claim 1, wherein the proximal portion of the retractor arm is retracted further into the lumen when in the retracted position than in the extended position, and is extended further from the distal end portion of the handle when in the extended position than in the retracted position.

9. The visualization tissue retractor according to claim 1, wherein the surgical camera assembly extends outwardly from the first or second face of the retractor arm and is laterally spaced from the side edges of the retractor arm.

10. The visualization tissue retractor according to claim 1, wherein a first axis is defined through the longitudinal length of the retractor arm and a second axis that is perpendicular to the first axis is defined through the first and second faces of the retractor arm, and the rotatable camera is configured to rotate through an angle extending along the second axis.

11. A system, comprising:
a portable display device; and
a visualization tissue retractor, including:
  a handle defining a proximal end portion and a distal end portion, the distal end portion defining a lumen therein;
  a dock extending from the proximal end portion of the handle, the dock configured to receive the portable display device;
  a retractor arm extending from the distal end portion of the handle, a proximal portion of the retractor arm slidably received within the lumen to enable the retractor arm to slide relative to the handle between a retracted position and an extended position, the retractor arm having opposed first and second faces, one of the first or second faces defining a guide track disposed on a central portion thereof in laterally spaced relation relative to side edges of the retractor arm and extending along at least a portion of a longitudinal length thereof; and
  a surgical camera assembly engaged with the guide track and configured to slide therealong, the surgical camera assembly including a rotatable surgical camera.

12. The system according to claim 11, wherein the surgical camera assembly is configured to communicate with the portable display device such that the portable display device displays a video feed from the rotatable surgical camera of the surgical camera assembly.

13. The system according to claim 11, wherein the portable display device is configured to enable a user to control operation of the surgical camera assembly from the portable display device.

14. The system according to claim 11, wherein the surgical camera assembly includes a light source.

15. The system according to claim 11, wherein the dock includes an electrical connection interface configured to electrically couple to the portable display device.

16. The system according to claim 11, wherein the retractor arm defines a generally U-shaped configuration with the first face of the retractor arm being at least partially concave and the second face of the retractor arm being at least partially convex, and wherein the guide track is disposed along a distal portion of the retractor arm on the second face thereof.

17. The system according to claim 11, wherein at least one of the handle or the surgical camera assembly includes a motor configured to drive movement of the surgical camera assembly along the guide track.

18. The system according to claim 11, wherein at least one of a battery of the handle, a battery of the surgical camera assembly, or the portable display device powers the surgical camera assembly.

19. The system according to claim 11, wherein the retractor arm includes indicia disposed thereon configured to indicate an insertion depth of the retractor arm to a user.

20. The system according to claim 11, wherein the proximal portion of the retractor arm is retracted further into the lumen when in the retracted position than in the extended position, and is extended further from the distal end portion of the handle when in the extended position than in the retracted position.

\* \* \* \* \*